US010711052B2

(12) United States Patent
Chen et al.

(10) Patent No.: US 10,711,052 B2
(45) Date of Patent: Jul. 14, 2020

(54) METHOD FOR PROMOTING WOUND HEALING

(71) Applicants: Mei Chen, Altadena, CA (US); David Woodley, Altadena, CA (US)

(72) Inventors: Mei Chen, Altadena, CA (US); David Woodley, Altadena, CA (US)

(73) Assignee: UNIVERSITY OF SOUTHERN CALIFORNIA, Los Angeles, CA (US)

(*) Notice: Subject to any disclaimer, the term of this patent is extended or adjusted under 35 U.S.C. 154(b) by 162 days.

(21) Appl. No.: 13/657,594

(22) Filed: Oct. 22, 2012

(65) Prior Publication Data

US 2013/0150305 A1    Jun. 13, 2013

Related U.S. Application Data

(62) Division of application No. 12/516,276, filed as application No. PCT/US2007/085754 on Nov. 28, 2007, now abandoned.

(60) Provisional application No. 60/867,560, filed on Nov. 28, 2006.

(51) Int. Cl.
    *A61K 38/39* (2006.01)
    *C07K 14/78* (2006.01)
    *A61K 31/70* (2006.01)

(52) U.S. Cl.
    CPC ............. *C07K 14/78* (2013.01); *A61K 31/70* (2013.01); *A61K 38/39* (2013.01)

(58) Field of Classification Search
    None
    See application file for complete search history.

(56) References Cited

U.S. PATENT DOCUMENTS

| 7,939,281 B2 * | 5/2011 | Wilkes ................. G01N 33/564 424/184.1 |
| 2003/0091547 A1 | 5/2003 | Edelberg et al. |
| 2003/0228292 A1 | 12/2003 | Gazit et al. |
| 2004/0037813 A1 * | 2/2004 | Simpson .................... A61F 2/08 424/93.7 |
| 2008/0188642 A1 * | 8/2008 | Ying et al. .................... 530/356 |
| 2014/0031295 A1 * | 1/2014 | Chen et al. .................. 514/17.2 |

FOREIGN PATENT DOCUMENTS

WO    WO 2005/014623    *    2/2005

OTHER PUBLICATIONS

Arbiser et al. Basic Fibroblast Growth Factor: A Missing Link between Collagen VII, Increased Collagenase, and Squamous Cell Carcinoma in Recessive Dystrophic Epidermolysis Bullosa. Molecular Medicine 4: 191-195 (1998).*

Chen et al. Intravenously injected recombinant human type VII collagen homes to skin wounds and promotes wound healing. Journal of Investigative Dermatology; Abstract. vol. 126, No. Suppl. 1, pp. 28. Meeting Info.: 67th Annual Meeting of the Society-for-Investigative-Dermatology. Philadelphia, PA, USA (Apr. 2006).*

Plenz et al. Vascular collagens: spotlight on the role of type VIII collagen in atherosclerosis. Atherogenesis166:1-11 (2003).*

Cooley, B.C. Collagen-induced Thrombosis in Murine Arteries and Veins, Thrombosis Research, 131:49-54 (2013).*

DiMinno, G. and Silver, M., Mouse Antithrombotic Assay: A Simple Method for the Evaluation of Antithrombotic Agents in Vivo. Potentiation of Antithrombotic Activity by Ethyl Alcohol, vol. 225. No. 1:57-60 (1983).*

Crikis, S. et al. Antiinflammatory and Anticoagulant Effects of Transgenic Expression of Human Thrombomodulin in Mice American Journal of Transplantation 10: 242-250 (2010).*

Woodley et al. Injection of recombinant human type VII collagen restores collagen function in dystrophic epidermolysis bullosa. Nature Medicine vol. 10/No. 7:693-695 (Jul. 2004).*

M. Chen, "Intravenously Injected Recombinant Human Type VII Collagen Homes to Skin Wounds and Promotes Wound Healing" Journal of Investigative Dermatology, vol. 126, No. Suppl. 1, p. 28, Apr. 2006.

Woodley et al., "Injection of Recombinant Human Type VII Collagen Restores Collagen Function in Dystrophic Epidermolysis Bullosa" NatMed, vol. 10, No. 7, pp. 693-695, Jul. 2004.

Ortiz-Urda et al., "Injection of Genetically Engineered Fibroblast Corrects Regenerated Human Epidermolysis Bullosa Skin Tissue" J. Clinical Investigation, vol. 111, No. 2, pp. 251-255, Jan. 2003.

D.T. Woodley, "Interdermal Injection of Lentiviral Vectors Corrects Regenerated Human Dystrophic Epidermalysis Bullosa Skin Tissue in Vivo" Molecular Therapy, vol. 10, No. 2, pp. 318-326, Aug. 2004.

Evangelos Badiavas et al., "Participation of Bone Marrow Derived Cells in Cutaneous Wound Healing" Journal of Cellular Physiology, vol. 196, pp. 245-520, 2003.

Ole Swensson, "Generalized Atrophic Benign Epidermolysis Bullosa in 2 Siblings Complicated by Multiple Squamous Cell Carcinomas" Arch Dermatol., vol. 134, pp. 199-203, 1998.

David Woodley et al., "Normal and Gene-Corrected Dystrophic Epidermolysis Bullosa Fibroblasts Alone Can Produce Type VII Collagen at the Basement Membrane Zone" Journal of Investigative Dermatology, vol. 121, pp. 1021-1028, 2003.

David Woodley et al., "Intradermal Injection of Lentiviral Vectors Corrects Regenerated Human Dystrophic Epidermolysis Bullosa Skin Tissue in Vivo" Molecular Therapy, vol. 10, No. 2, pp. 318-326, Aug. 2004.

(Continued)

*Primary Examiner* — Elizabeth C. Kemmerer
*Assistant Examiner* — Regina M DeBerry
(74) *Attorney, Agent, or Firm* — Greer, Burns & Crain, Ltd.; Gregory P. Einhorn (57) ABSTRACT

The present invention discloses a method for treating wounds and for accelerating the healing of wounds by administering an effective amount of a pharmaceutical composition containing type VII collagen protein, mini-C7 protein, variants thereof or any combinations thereof. The pharmaceutical composition may be administered through a variety of routes including intravenous injection, topical application, or oral ingestion. The method may further include administering a genetically modified fibroblast capable of expressing type VII collagen protein, mini-C7 protein, variants thereof or small growth factors to achieve synergistic healing effect.

14 Claims, 9 Drawing Sheets

(56) References Cited

OTHER PUBLICATIONS

Denyer J, Pillay E., "Best Practice Guidelines for Skin and Wound Care in Epidermolysis Bullosa," A Wound's International publication, www.woundsinternational.com, International Concensus, DEBRA, 2012., pp. 1-44.
Daley, "Wound Care Treatment & Management," http://emedicine.medscape.com/article/194018-treatment), Oct. 22, 2015, pp. 1-10.
Humira; Highlights of Prescribing information; Revised: Dec. 2011.
Accutane®, (isotretinoin capsules); Roche Laboratories Inc.; Jan. 2010; pp. 1-42.
Zyderm; Warning Precautions; RxList, The Internet Drug Index; http://www.rxlist.com/zyderm-drug/warnings-precautions.htm, RxList, Inc., 2016; pp. 1-2.
Bergmeier et al.; "Extracellular Matrix Proteins in Hemostasis and Thrombosis", Cold Spring Harb Perspect Biol. Feb. 1, 2012;4(2), 8.
Extended European Search Report dated Jul. 22, 2019, regarding EP 19 17 1618.
Chen, Mei and Woodley, David T.: *Fibroblasts as Target Cells for DEB Gene Therapy*; J. of Investigative Dermatology, vol. 126, pp. 708-710, (2006).
Chen, Mei et al.: *Development and Characterization of a Recombinant Truncated Type VII Collagen "Minigene"*; Journal of Biological Chemistry, vol. 275, No. 32, pp. 24429-24435, Aug. 11, 2000.
Huang, Y. et al.: *"Intravenously Injected Gene-Corrected Dystrophic Epidermolysis Bullosa (DEB) Fibroblasts Home to Skin Wounds: Implications for DEB Treatment"*; Proceedings from the University of Southern California, Dept. of Dermatology, Apr. 2005, Los Angeles, CA, Abstract 486.

\* cited by examiner

METHOD FOR PROMOTING WOUND HEALING

CROSS-REFERENCE TO RELATED APPLICATIONS

This application is a divisional application of U.S. Ser. No. 12/516,276, filed Mar. 22, 2010, now abandoned which is a 371 of PCT/US07/85754, filed Nov. 28, 2007 which claims an invention which was disclosed in U.S. Provisional Application No. 60/867,560, filed Nov. 28, 2006, entitled "INTRAVENOUS TYPE VII (ANCHORING FIBRIL) COLLAGEN TO PROMOTE CUTANEOUS WOUNDS HEALING". The benefit under PCT Article 8 is hereby claimed. The above priority application is hereby incorporated herein by reference.

STATEMENT OF FEDERALLY SPONSORED RESEARCH AND DEVELOPMENT

This invention was made, at least in part, with Government support under NIH grants RO-I AR 33625-22 and RO-I AR 47981-7. The Government has certain rights in the invention.

FIELD OF THE INVENTION

The present invention relates generally to wound healing. In particular, the present invention relates to methods for healing wounds, and improving the appearance of photo-aged and photo-damaged skin. The present invention also relates to recombinant type VII collagen and methods for producing and using thereof.

BACKGROUND OF THE INVENTION

Healing wounds in human skins is a major medical problem, particularly in the elderly patient population. According to the Wound Healing Society, about 15% of older adults suffer from chronic, hard-to-heal wounds [1]. It is also estimated that about 18% of diabetic patients over the age of 65 years will have chronic, nonhealing skin ulcers [2]. To improve the healing process, researchers have been considering topically applying epidermal growth factor as a promising therapy. This therapy has been shown to accelerate wound closure of acute wounds in patients [3-5]. However, due to the high cost and other practical considerations, this strategy has not been commercially viable as a general solution for wound healing. So far, only platelet-derived growth factor has been approved by the Federal Drug Administration for treatment of nonhealing diabetic foot ulcers. Even with this therapy, practitioners have found it to be limiting and not always successful. One difficulty associated with the topical application of growth factors is that the wound bed is often laden with proteolytic enzymes which tend to degrade and nullify the applied agent.

To investigate better approaches of skin wound healing, various models of skin diseases have been used. In particular, a genetically inherited skin disease known as Dystrophic forms of Epidermolysis Bullosa (DEB) in children has provided valuable insights.

DEB is an incurable genetic disease caused by a gene defect in the gene that encodes for type VII collagen. Children who suffer from DEB are born with skin fragility, blistering, and repeated wounding and healing of their skin wounds [6]. In these children, their wounds will typically heal with fibrosis, scarring, and small epidermal inclusion cysts called milia. Because the outer epidermal layer of the DEB patient adheres poorly to the underlying dermal connective tissue, even the slightest trauma will cause epidermal-dermal disadherence. Therefore, DEB patients suffer from chronic skin wounds. Studies have found that the poor skin adherence is due to a defect in the gene which encodes for type VII (anchoring fibril) collagen (C7); a protein that serves to anchor the epidermis onto the dermis [7,8].

At the molecular level, C7 is composed of three identical alpha chains, each consisting of a 145-kDa central collagenous triple-helical segment, flanked by a large 145-kDa amino-terminal, non-collagenous domain (NC1), and a small 34-kDa carboxyl-terminal non-collagenous domain (NC2) [9,10]. Within the extracellular space, C7 molecules form antiparallel dimers which aggregate laterally to form anchoring fibrils. In normal skin, C7 forms anchoring fibrils ranging from about 200-700 nm in size that emanate from epidermal-dermal junction (EDJ) and extend perpendicularly down into the papillary dermis. In DEB patients, the EDJ is characterized by a paucity of normal anchoring fibrils. Based on the underlying etiology of the disease, one logical approach for treating the disease is to correct the genetic defect through gene therapy.

There are several recent studies related to ex vivo gene therapy for DEB. In the study by Oritz-Urda et at., COL7A1 cDNA was successfully and stably integrated into C7-null keratinocytes from recessive DEB (RDEB) patients using a phi C31 integrase-based non-viral gene transfer approach. By transplanting a human skin equivalent comprising these gene-corrected cells onto severe combined immunodeficient (SCID) mice, they showed that many of the RDEB features were corrected after gene transfer In another study by the inventors of the present invention, a minimal lentiviral vector was developed to express C7 in RDEB keratinocytes and fibroblasts (in which C7 was absent). This construct was subsequently used to demonstrate the reversion of the RDEB cellular phenotype [12]. In this experiment, the gene-corrected RDEB cells and native un-corrected RDEB cells were used to create a composite human skin equivalent which was then transplanted onto SCID mice. It was shown that the transplanted human skin made with the gene-corrected RDEB cells (but not the control un-corrected RDEB cells) exhibited C7 at the EDJ and the RDEB skin phenotype was corrected. Moreover, in the skin equivalents composed of gene-corrected (but not gene-uncorrected) cells, the transgene-derived C7 also created anchoring fibril structures that were correctly organized into the basement membrane zone (BMZ) lying between the epidermis and dermis.

However, this type of ex vivo approach requires transplantation of gene-corrected cells onto surgically prepared sites of the patient's skin. The experience of using cultured keratinocyte autografts for transplantation onto human wounds had shown that this technology is often fraught with technical difficulties and poor graft take. Therefore, although this ex vivo type of therapy (i.e. gene correcting cells in culture and then transplanting them back as skin equivalents onto the DEB patient) is theoretically possible, the technical hurdles make it in-efficient, logistically difficult, expensive, labor-intensive and of limited efficacy.

As an alternative approach, a more straightforward "direct in vivo gene therapy" was developed. With this approach, DEB wounded skin is directly injected through intradermal injection with gene-corrected RDEB fibroblasts. The gene-corrected intradermally injected cells then set up residence in the DEB skin and synthesize and secrete C7 which is lacking in the DEB skin. Surprisingly, the secreted C7 in the extracellular dermal tissue, binds to the BMZ of the DEB skin and correctly organizes into anchoring fibril structures. Now, the DEB skin which previously lacked C7 and anchoring fibrils, now has these elements and the DEB skin phenotype is corrected. The poor epidermal-dermal adherence is now corrected. This is called "cell therapy" for DEB by the inventors. The inventors also showed that the same events would occur if they intradermally injected full-length or "mini-C7" into DEB skin, the injected C7 would bind to the BMZ of the DEB skin and form correctly-organized anchoring fibrils and correct the DEB skin phenotype. The inventors called this "protein therapy" for DEB.

Full-length C7 contains a 39 amino acid interruption in the helical sequence which forms site that is highly susceptible to degradation by protease. The mini-C7 was designed by the inventors to contain the intact noncollagenous domains, NC1 and NC2, and half of the central collagenous domain. By excluding the 39 amino acid interrupt, this mini-C7 is made highly stable. The enhanced stability of mini-C7 over native C7 may better withstand proteolytic digestion in RDEB wounds and provide a more sustained gene product in patients. The inventors have shown that the mini-C7 is highly resistant to proteolytic digestion and yet when injected into DEB skin behaves identically to the full-length C7 in that it will bind to the BMZ, create new anchoring fibril structures and correct the DEB skin phenotype. Thirdly, the inventors showed that rather than intradermally injecting RDEB gene-corrected cells or C7 itself into DEB skin, they could inject simply into the DEB skin the lentiviral vector expressing either the full-length C7 or mini-C7. In this case, the exogenously injected vector was taken up by the endogenous dermal fibroblasts within the dermis of the DEB skin. These endogenous fibroblasts which previously lacked the ability to make C7 or mini-C7, now could synthesize and secrete these large proteins into the dermal extracellular environment. There, the C7 or mini-C7 homed to the BMZ of the DEB skin, organized into anchoring fibril structures and corrected the DEB skin phenotype. The inventors called this "vector therapy" for DEB [13-16, the relevant portions thereof are incorporated herein by reference].

In recent experiments, the inventors have shown that the intradermal approach is highly efficient if the agents are delivered in the high papillary dermis using a 30 guage needle with the bevel oriented upward, using a volume between 2 microliters and 2 milliters and injected into four quadrants of DEB skin between 1×1 cm and 6×6 cm.

In a more recent study, the investigators evaluated the feasibility of protein therapy in a C7 null DEB mouse which recapitulates the clinical and ultrastructural features of human RDEB. The investigators intradermally injected purified human C7 (into the new born DEB mice with severe skin blistering and fragility and found that the injected human C7 transported and stably incorporated into the mouse's BMZ and formed anchoring fibrils. The restoration of C7 corrected the DEB murine phenotype as demonstrated by decreased skin fragility and blistering, reduced new blister formation and marked prolonged survival.

Despite the above mentioned advances, there are still no effective methods for treating DEB. Because patients with severe DEB have widespread lesions and multiple wounds spanning large areas of trauma-prone sites such as the sacrum, hips, feet, mouth, scalp, lower back and hands, the treatment of such DEB patients via any of the three above outlined direct intradermal injection approaches would require numerous injections into multiple wound sites. Accordingly, intradermal injections of the therapeutic agents outlined above (gene-corrected cells, recombinant forms of C7 or C7 expressing vectors) would require site-specific treatment of each and every wound by one or more intradermal injections. While this is doable, such a cumbersome method of treatment still leaves much to be desired. It would be ideal to offer patients with DEB or patients with multiple wounds a single therapy that will require only a single route of delivery but that will "home" to all of the wounds automatically upon delivery to correct the skin wounds located at scattered sites.

Therefore, there still exists a great need for better method of treating skin wounds in general and DEB in particular.

SUMMARY OF THE INVENTION

Accordingly, it is an object of the present invention to provide effective methods and therapeutic agents for treating DEB that avoids the problems of other methods in the art.

It is a further object of the present invention to provide a method that is generally applicable to promote healing of all skin wounds that has the characteristics of being safe, effective, and easy to administer.

These and other objects of the present invention are realized through the surprising discovery that C7, mini-C7, and variants thereof have the ability to "home" to wound sites without requiring a delivery vehicle such as a genetically engineered fibroblast. In light of the difficulties in treating DEB5 this discovery provides a basis for methods and therapeutic agents that can promote wound healing in DEB patients without the limitations of the existing methods in the art. Because the wound healing property of C7 is not only limited to patients suffering from DEB, the present invention is also applicable generally to all types of skin wound healing.

Therefore, in one aspect, the present invention provides a method for treating and accelerating skin wound healing in a subject, having the general steps of: administering to the subject an effective amount of a pharmaceutical composition comprising essentially of C7, mini-C7, or a variant thereof.

It is also a surprising discovery of the present invention that the ability of C7 and its variants to "home" to the wound sites are not dependent on any particular route of administration. For example, whether C7 is administered through intravenous injection or topical application, the healing effect remains.

In a further embodiment of the present invention, a method of treating or accelerating wound healing in a subject may further comprise method steps that utilize a wound site targeting vehicle such as a genetically engineered fibroblast. In this manner, combinations of topical application of C7 and IV injection of fibroblasts may synergistically serve to enhance the outcome of the treatment. This can be understood by recognizing the fact that directly applied C7 and variants thereof are subject to the host's metabolism and will require repeated application whereas genetically engineered fibroblasts will constantly secret C7 and other beneficial agents for as long as it survives in the host. Therefore, a method combining both approaches may benefit from the immediate bioavailability of direct application while still enjoying the constant and extended release of pharmaceutically active agents through gene product expression of genetically engineered fibroblasts.

Other aspects and advantages of the invention will be apparent from the following description and the appended claims.

DETAILED DESCRIPTION

In the copending PCT application U.S. Ser. No. 07/85754, we have disclosed a method of delivering C7 to the wound sites by using a genetically modified fibroblast as a delivery vehicle. In this invention, we have further discovered that C7, mini-C7, and variants thereof are capable of "homing" to wound sites without the need of a delivery vehicle. Thus, it is an unexpected discovery of the present invention that C7, mini-C7, and variants thereof all have the ability to home to remote wound sites regardless of the method of administration (e.g. intravenous injection, intradermal injection, topical application etc.).

Based on this discovery, the inventors of the present invention have developed methods for correcting the pathological condition of DEB, which is an incurable disease of children due to a genetic defect in the gene that encodes for type VII collagen. Methods in accordance with embodiments of the present invention are easy to operate, effective and do not suffer from the common problems of other methods in the art.

New modalities of therapeutic methods and agents based on the discovery of the present invention as outlined herein are clearly advantageous to other approaches of DEB gene-therapy in the art. For example, based on previous observations that gene-corrected RDEB keratinocytes alone can be used to restore C7 expression and anchoring fibril formation in vivo [11,12], grafting gene-corrected keratinocytes to the wounded sites was proposed. Although grafting gene-corrected epidermal autografts onto RDEB patients may be feasible, the procedure has many technical problems similar to those encountered when transplanting epidermal autografts onto burn wounds. Among the numerous technical difficulties, the degree of autograft take has been a major concern since approximately 40% of cultured epidermal autografts transplanted onto burn wounds do not take. Furthermore, the grafting procedure requires surgical excision of the patient's skin down to fascia for optimal autograft take [20-22]. As such, pain, immobilization of the patient, scarring, extensive wound care, and other potential morbidity issues severely limit the success of this strategy.

As an alternative approach, the direct intradermal injection of gene-corrected RDEB fibroblasts, recombinant C7, or lentiviral vectors expressing C7 for the correction of DEB was proposed. It had been shown that the intradermal injection of various therapeutic agents including cells, proteins, or lentivectors into intact RDEB skin stably restored C7 expression and anchoring fibrils at the BMZ and resulted in correction of the RDEB disease features. This approach was more advantageous over grafting thin-cultured epidermal autografts onto wounds because no surgery or grafting was required [13-16]. However, the small diffusion radius of intradermally injected agents and the inaccessibility of some sites such as the esophagus severely limit the applicability of intradermal injection therapies. Patients with generalized, extensive blistering wounds would require many intradermal injections at multiple sites. These issues pose practical and logistical concerns for the clinical use of intradermal injections for RDEB patients or patients with multiple wounds.

Further to the discovery that IV injected fibroblasts can specifically traffick to wounded skin, synthesize, and deposit human C7 at the newly formed BMZ of the host's skin, it was also found that C7, mmi-C7, and variants thereof also have the ability to "home" specifically to wound sites.

Accordingly, in one aspect, the present invention provides a method for treating or promoting healing of a skin wound in a subject having the general steps of: administering to the subject a pharmaceutical composition comprising essentially of C7, mini-C7, a variant thereof, or a combination thereof.

For the purpose of the present invention, the step of administering can be performed by any conventional or future developed means of delivering the pharmaceutical composition to the subject. Those skilled in the art will recognize that selection of the particular method for administering the pharmaceutical composition will depend on the specific embodiment of the pharmaceutical composition. For example, in cases where the pharmaceutical composition is in the form of a cream, an appropriate method of administering the composition would be to apply the composition topically to the subject. Other exemplary methods of administering the pharmaceutical composition may include intravenous injection, intradermal injection, or any other means of administering a pharmaceutical composition commonly known in the art.

For the purpose of the present invention, the pharmaceutical composition may be formulated in any form commonly known in the pharmaceutical art. For example, C7, and mini-C7 may be formulated as injectable liquid solutions, topical creams, rehydratable powder, encapulsated in microcapsules for extended release, inhalable fine particles, or as biosorbable patches. Numerous additives may also be suitably and beneficially added without affecting the effectiveness of the proteins. For example, a stabilizing agent may be added in a composition containing C7 to protect C7 from being degraded by proteases.

In some embodiments, methods of the present invention may further comprise a step of administering a genetically engineered fibroblast. As disclosed in the copending application, fibroblast cells may be genetically engineered to overexpress certain proteins beneficial to wound healing, including Cl, mini-C7, and other small growth factors. In these embodiments, the combination of Cell Therapy and Protein Therapy will further enhance the effectiveness of the treatment to suit different treatment requirements. In other words, molecularly engineered fibroblasts that synthesize and express C7, mini-C7, type I collagen, type III collagen, type XVII collagen, a small growth factor, a variant thereof, and combinations thereof, may be administered in several ways depending upon the patient's condition and number of wounds. Exemplary small growth factors may include epidermal growth factor (EGF), transforming growth factor alpha (TGF alpha), transforming growth factor beta (TGF beta), platelet derived growth factor (PDGF), or a combination thereof. These administration methods would include intravenous administration, topical administration, intradermal administration, and oral ingestion. For example, if the patient was a severe DEB patient with hundreds of wounds, the patient would likely be treated with intravenous recombinant C7 collagen in the short-run and then followed with intravenous injection of engineered fibroblasts later. If, on the other hand, the patient only had one or two lesions, the clinician would likely opt for topical or intradermal C7 treatment.

In general, methods in accordance with embodiments of the present invention are not limited to just treating skin wounds or genetic skin disorders, but are preferably suited to accelerate would healing in all types of wounds including chronic skinwounds, wounds caused by spinal cord injuries and strokes, or diabetes, but are not limited thereto. Exemplary chronic wounds may include stasis dermatitis leg ulcers, pressure decubitus ulcers, and diabetic trophic ulcers. Application for certain internal organ wounds and aging related skin damage or degradation may also be treated. For example, inflammatory bowel diseases, muscles, ligaments, photo-aging of skin etc. are also contemplated.

Having generally described this invention, a further understanding can be obtained by reference to the accompanying Figures and the following detailed explanations of the Figures.

Figure 1A:
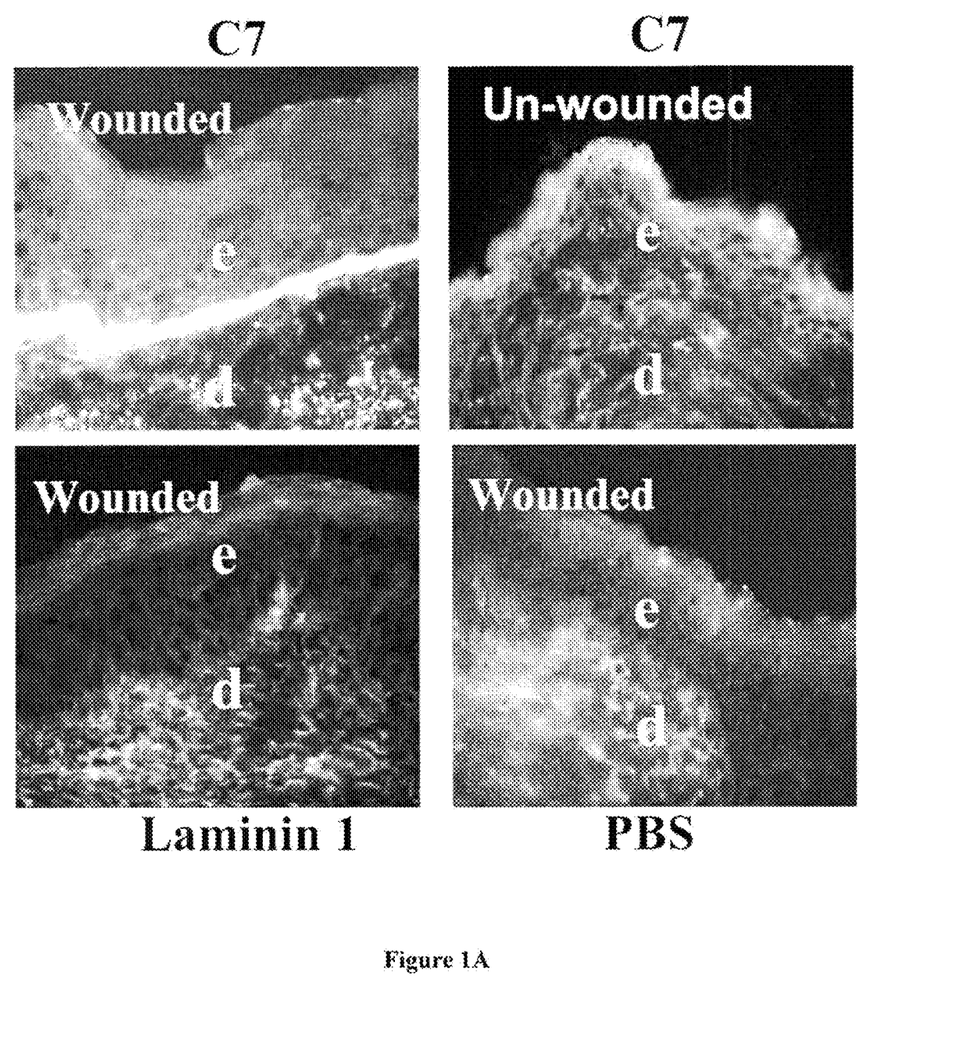
FIG. 1A shows immunofluorescent images of skin C7 staining on wound or unwound sites of mice IV injected with C7 and various other proteins.

Referring first to FIG. 1, there is shown the result of an experiment in which human C7 is injected intravenously to athymic nude mouse that had been wounded on the back by a standard 1 cm by 1 cm full-thickness wound. It was found that human C7 homed to the skin wound and incorporated into the mouse's regenerated BMZ. Figure IA shows immunofluorescence staining of the mouse's skin after IV injection of various proteins was performed with antibodies specific for human C7 at 2 weeks after the injection. Note that the IV injected C7 (panel A) homed and incorporated into the mouse's regenerated BMZ in wounded sites, but not in un-wounded sites (panel B). Further, there was no human C7 detected in mice who were injected with laminin 1 or PBS (panels C and D). This demonstrates that IV injected C7 is capable of homing to wound sites and promote wound healing.

Figure 1B:
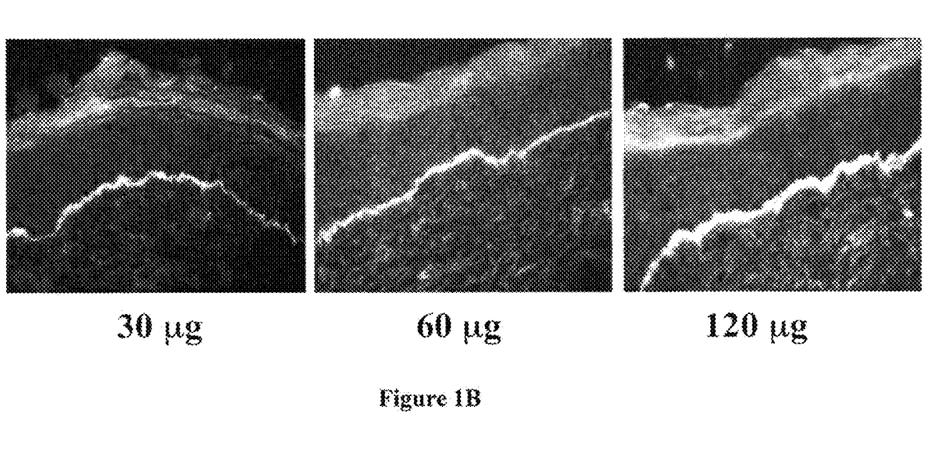
FIG. 1B shows dose-dependent deposition of human C7 at the mouse's BMZ after IV injection with C7.

FIG. 1B shows dose-dependent deposition of human C7 at the mouse's BMZ after IV injection with C7. Immunofluorescence staining with an antibody specific for human C7 was performed on healed mouse skin wounds after the animals were injected with 30 µg (A), 60 µg (B), and 120 µg (C) of C7 respectively. Note the dose-dependent increase in the deposition of human C7 at the mouse BMZ. This result indicates that C7 will home and become accumulated at the wound site.

Figure 2:
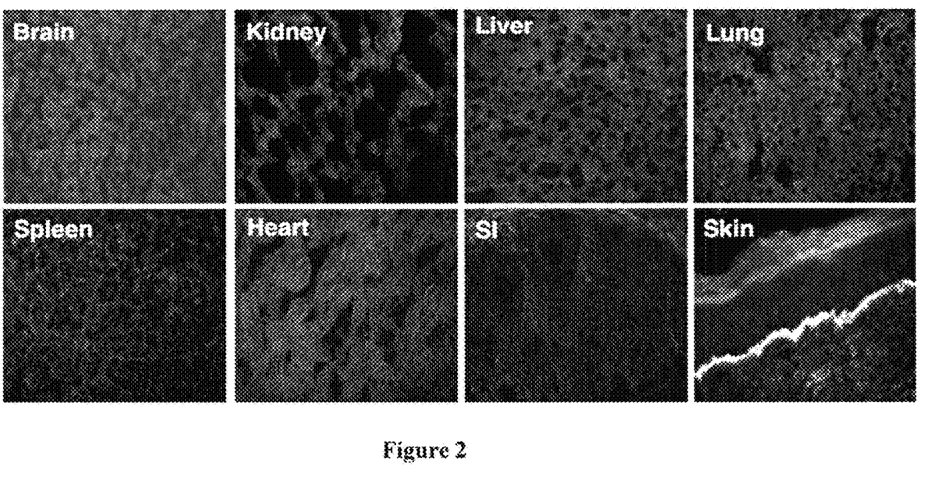
FIG. 2 shows immunofluorescent images of C7 distribution in various organs of a mouse after IV C7 injection.

Refer now to FIG. 2, there is shown the distribution of IV injected C7 found in various organs. Four weeks after IV injection of human C7, necropsies were performed on the mice (n=20 mice) and tissue sections obtained from brain, kidney, liver, lung, spleen, heart, small intestine, and healed skin were subjected to immunostaining using an antibody specific for human C7. Note that the injected C7 was readily detected in the BMZ of the wounded mouse's skin, but not in any other organs.

Figure 3A:
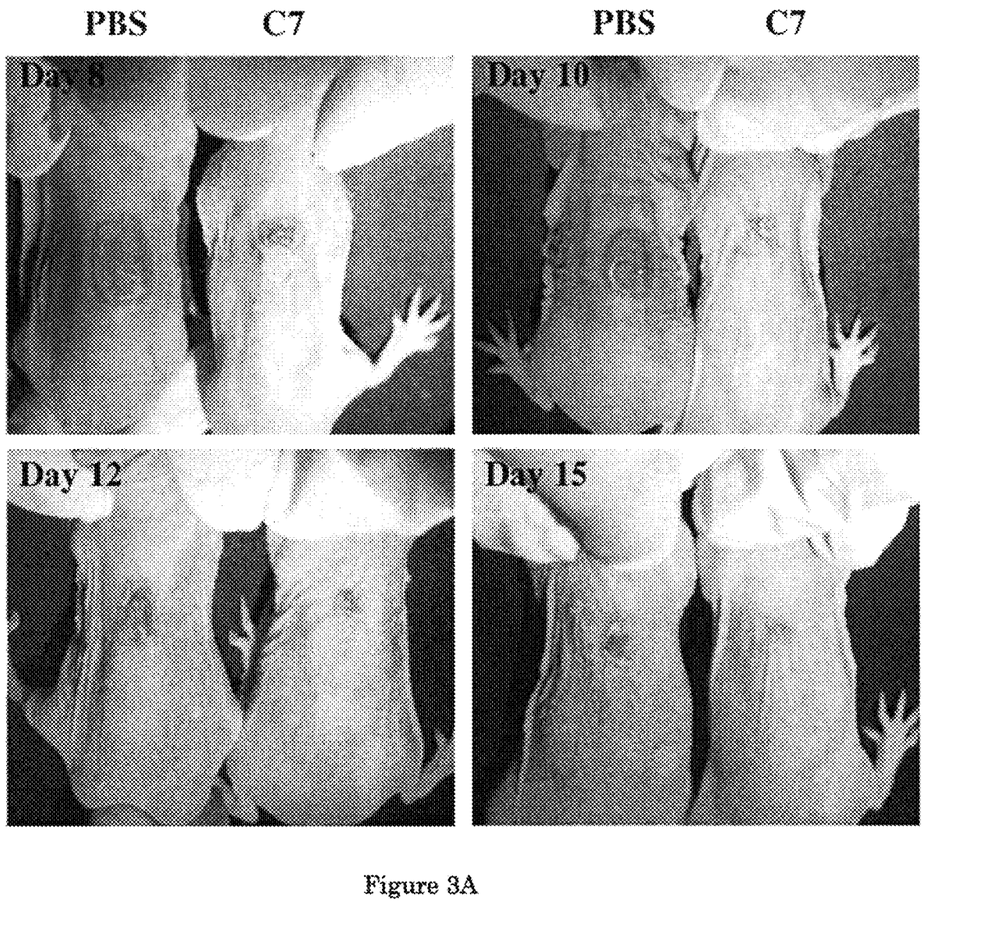
FIG. 3A shows that IV injected C7 promoted wound healing in mouse skin.
Figure 3B:
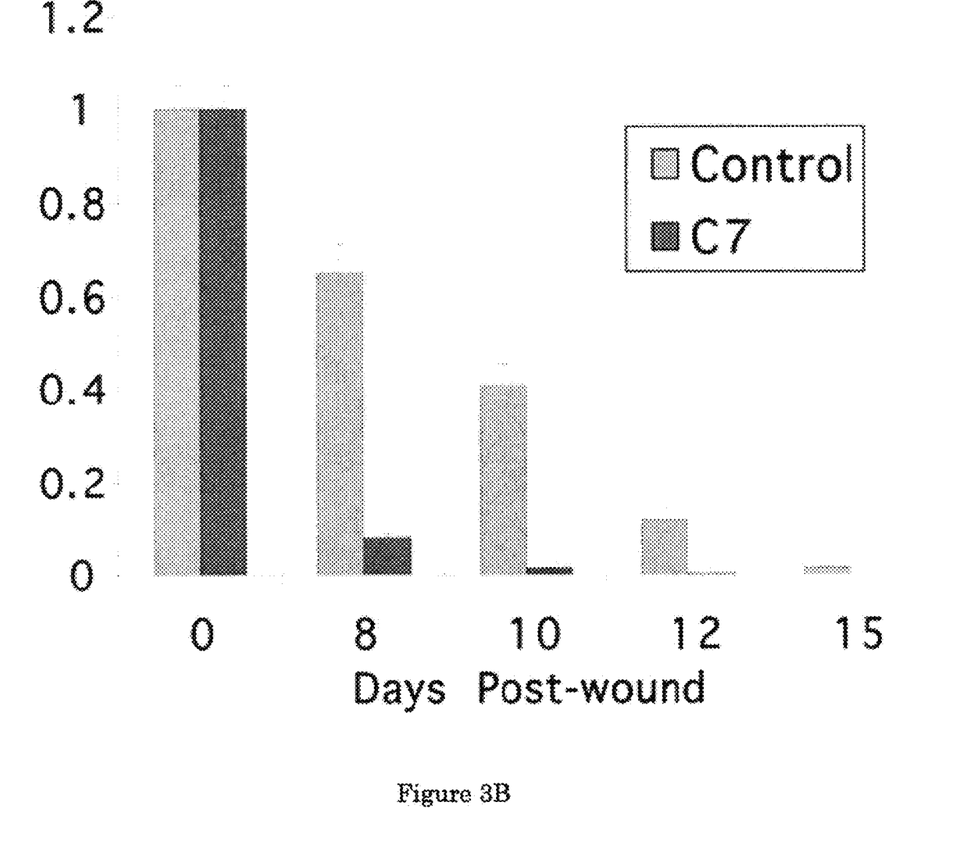
FIG. 3B shows a graphical comparison of the mean sizes of the wounds over the course of 15 days.

FIG. 3 shows a time course comparison of wound healing in two mice, one treated with C7, the other treated with PBS. In this experiment, a 1.0-cm² (1 cm×1 cm) square full-thickness excision wound was made on the mid-back of 8 to 10 week old athymic nude mice and then injected intravenously 8 hours after wounding with 100 [mu]g human C7 or PBS (n=10 mice per group). FIG. 3A shows a representative image of wounds on mice at day 8, 10, 12, and 15. Wound sizes were significantly reduced in mice injected with C7 compared with mice that were injected with PBS at 8, 10 and 12 days after wounding. A graphical comparison of the mean sizes of the wounds (mean±SD) over the course of 15 days is shown in FIG. 3B. Wound sizes were measured at day 0, 8, 10, 12, and 15 post-wounding (n=10 mice for each group). From this analysis, the wound healing effect of C7 is clearly demonstrated.

Figure 4A:
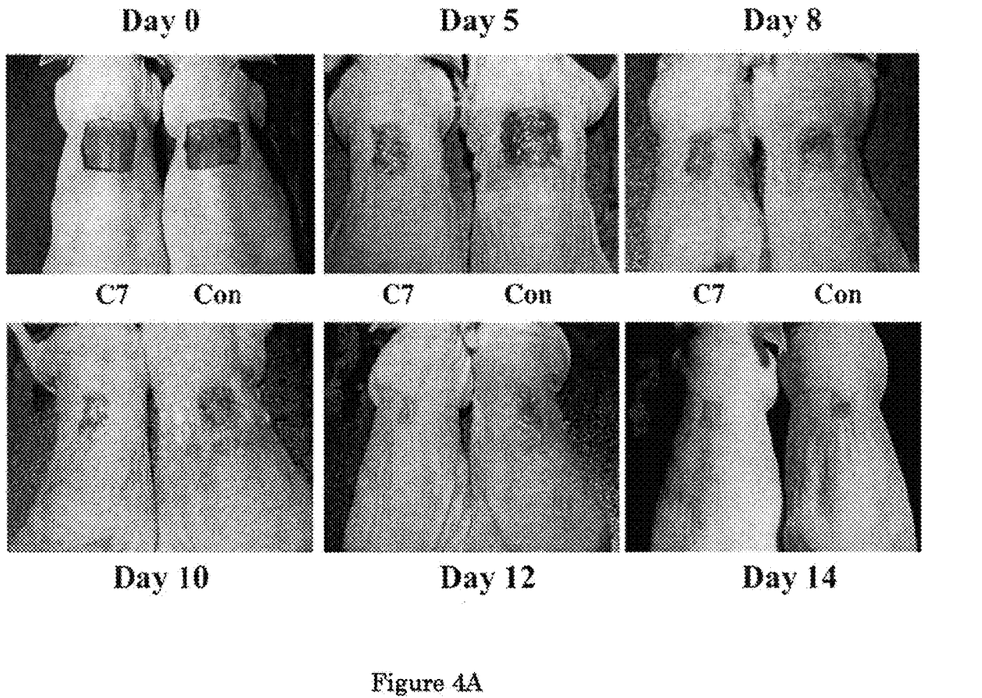
FIG. 4A shows that topical application of C7 enhances wound healing in mice.
Figure 4B:
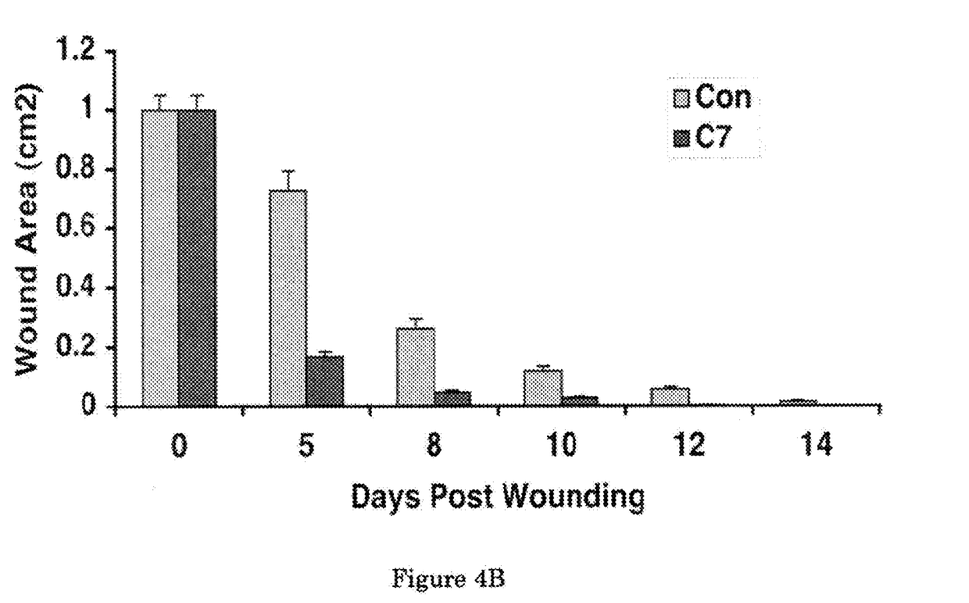
FIG. 4B shows a graphical comparison of the mean sizes of the wounds over the course of 14 days.

Referring now to FIG. 4, the effect of applying C7 topically was also investigated. In this experiment, a 1.0-cm² (1 cm×1 cm) square full-thickness excision wound was made on the mid-back of 8 to 10 week old athymic nude mice. Human recombinant C7 (40 [mu]g) was applied topically daily for 2 days (n=10 mice per group). FIG. 4A shows representative images of would sizes on day 0, 5, 8, 10, 12 and 14. It can be seen from these images that wound sizes were significantly reduced in mice topically treated with the cream containing C7 (C7), but not the cream alone (Con). A graphical comparison of the mean sizes of the wounds (mean±SD) over the course of 14 days is shown in FIG. 4B. Wound sizes were measured at day 0, 5, 8, 10, 12 and 14 post-wounding (n=10 mice for each group).

Figure 5A:
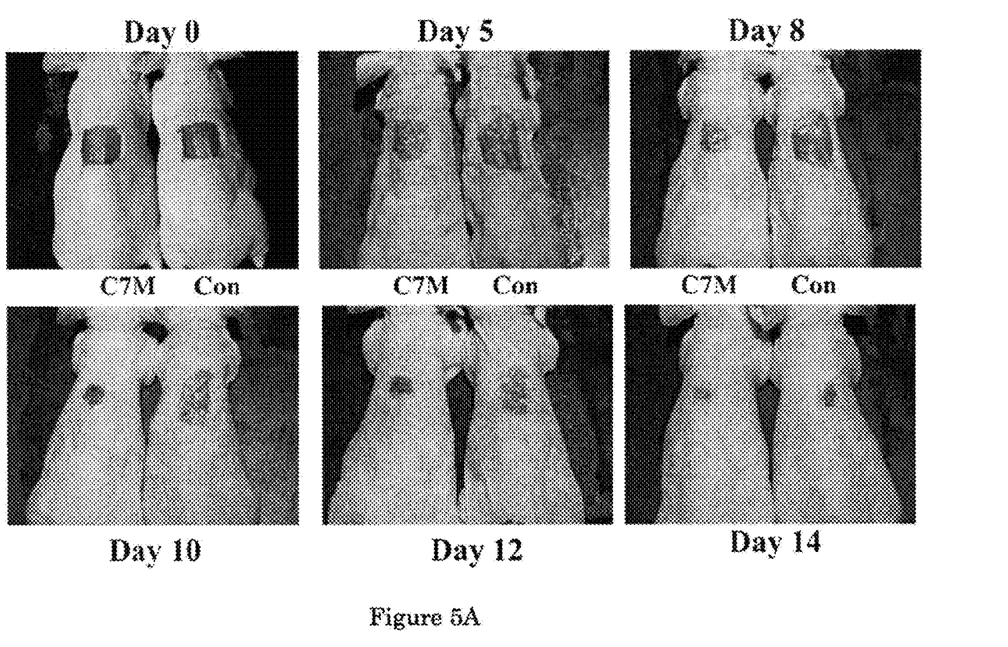
FIG. 5A shows that topical application of Mini-C7 enhances wound healing in mice.
Figure 5B:
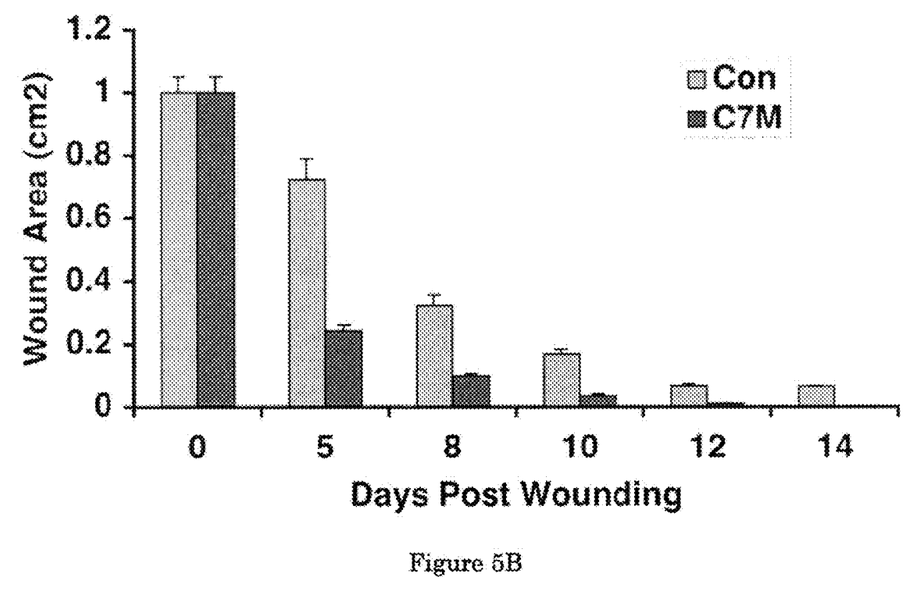
FIG. 5B shows a graphical comparison of the mean wound sizes over the course of 14 days.

Referring now to FIG. 5, a similarly experiment as in FIG. 4 was conducted using mini-C7 instead of C7. A 1.0-cm² (1 cm×1 cm) square full-thickness excision wound was made on the mid-back of 8 to 10 week old athymic nude mice and human recombinant mini-C7 (40 µg) was applied topically daily for 2 days (n=10 mice per group). FIG. 5A shows representative images of wounds on day 0, 5, 8, 10, 12 and 14. Wound sizes were significantly reduced in mice topically treated with the cream containing mini-C7 (C7M), but not the cream alone (Con). A graphical comparison of the mean wound sizes (mean±SD) is shown in FIG. 5B. Wound sizes were measured at day 0, 5, 8, 10, 12 and 14 post-wounding (n=10 mice for each group).

Comparing FIG. 4B to 5B, it can be seen that the wound healing effect of mini-C7 is qualitatively identical to C7.

It will be understood by those skilled in the art that the foregoing description and Figures are provided for the sole purpose of illustration only and should not be construed as limiting. For this reason, the scope of the present invention is as defined in the accompanying claims.

REFERENCES

1. Stein, J Chronic wounds on the rise. Internal Medicine World Report 2000, p.
2. Hess, C T (1999). Care for a diabetic ulcer. Nursing 29: 71.
3. Brown, G L et al. (1989). Enhancement of wound healing by topical treatment with epidermal growth factor. N Engl J Med 321:76-79.
4. Goldman, R (2004). Adv Skin Wound Care 17: 24. Review.
5. Fu, X, Li, X, Cheng, B, Chen, W and Sheng, Z (2005). Engineered growth factors and cutaneous wound healing: success and possible questions in the past 10 years. Wound Repair Regen 13: 122-130.
6. Lin, A N and Carter, D M (eds) (1992). Epidermolysis Bullosa: Basic and Clinical Aspects.Springer-Verlag Inc.: NY.
7. Briggaman, R A and Wheeler Jr, C E (1975). The epidermal-dermal junction. J Invest Dermatol 65: 71-84.
8. Uitto, J and Christiano, A M (1994). Molecular basis for the dystrophic forms of epidermolysis bullosa: mutations in the type VII collagen gene. Arch Dermatol Res 287: 16-22.

9. Burgeson, R E (1993). Type VII collagen, anchoring fibrils, and epidermolysis bullosa. J Invest Dermatol 101: 252-255.
10. Sakai, L Y, Keene, D R, Morris, N P and Burgeson, R E (1986). Type VII collagen is a major structural component of anchoring fibrils. J Cell Biol 103: 1577-1586.
11. Ortiz-Urda, S et al. (2002). Stable nonviral genetic correction of inherited human skin disease. Nat Med 8: 1166-1170.
12. Chen, M et al. (2002). Restoration of type VII collagen expression and function in dystrophic epidermolysis bullosa. Nat Genet 32: 670-675.
13. Woodley, D T et al. (2003). Normal and gene-corrected dystrophic epidermolysis bullosa fibroblasts alone can produce type VII collagen at the basement membrane zone. J Invest Dermatol 121: 1021-1028.
14. Ortiz-Urda, S, Lin, Q, Green, C L, Keene, D R, Marinkovich, M P and Khavari, P A (2003). Injection of genetically engineered fibroblasts corrects regenerated human epidermolysis bullosa skin tissue. J Clin Invest 111:251-255.
15. Woodley, D T et al. (2004). Intradermal injection of lentiviral vectors corrects regenerated human dystrophic epidermolysis bullosa skin tissue in vivo. Mol Ther 10: 318-326.
16. Woodley, D T et al. (2004). Injection of recombinant human type VII collagen restores collagen function in dystrophic epidermolysis bullosa. Nat Med 10:693-695.
17. Singer, A J and Clark, R A F (1999). Cutaneous wound healing. Rev N Engl J Med 341:738-746.
18. Li3 W, Fan, J, Chen, M and Woodley, D T (2004). Mechanisms of human skin cell motility. Histol Histopathol 19: 1311-1324.
19. Kim, Y H, Woodley, D T, Wynn, K C, Giomi, W and Bauer, E A (1992). Recessive dystrohpic bullosa phenotype is preserved in xenografts using SCID mice: development of an experimental in vivo model. J Invest Dermatol 92: 191-197.
20. Gallico III, G G, O'Connor, N E, Compton, C C, Kehinde, 0 and Green, H (1984). Permanent coverage of large burn wounds with autologous cultured human epithelium. N Engl J Med 311:448-51.
21. Herzog, S R, Meyer, A, Woodley, D T and Peterson, H D (1988). Wound coverage with cultured autologous keratinocytes: use after burn wound excision, including biopsy folio wup. J Trauma 28: 195-198.
22. Woodley, D T et al, (1988). Bound wound resurfaced by cultured epidermal autografts show abnormal reconstitution of anchoring fibrils. JAMA 259: 2566-2571.
23. Badiavas, E V, Abedi, M, Butmaarc, J, Falanga, J V and Quesenberry, P (2003). Participation of bone marrow derived cells in cutaneous wounding healing. J Cell Physiol 196: 245-250.
24. Badiavas, E V and Falanga, V (2003). Treatment of chronic wounds with bone marrow-derived cells. Arch Dermatol 139: 510-516.
25. Fathke, C et al. (2004). Contribution of bone marrow-derived cells to skin: collagen deposition and wound repair. Stem Cells 22: 812-822.
26. Ito, M et al. (2005). Stem cells in the hair follicle bulge contribute to wound repair but not to homeostasis of the epidermis. Nat Med 11: 1351-1354.
27. Chen, M, O'Toole, E A, Li, Y Y and Woodley, D T (1999). a2b1 integrin mediates dermal fibroblast attachment to type VII collagen via a 158 amino acid segment of the NC1 domain. Exp Cell Res 249: 231-239.
28. Haapasalmi, K et al. (1995). Expression of epithelial adhesion proteins and integrins in chronic inflammation. Am J Pathol 147: 193-206.
29. Woodley, D T, Peterson, H D and Herzog, S R. (1988). Burn wounds resurfaced by cultured epidermal autografts show abnormal reconstitution of anchoring fibrils. JAMA 259:2566-2571.
30. Chen, M et al. (1997). Interactions of the amino-terminal noncollagenous (NC1) domain of type WI collagen with extracellular matrix components. J Biol Chem 272: 14516-14522.
31. Chen, M, Marinkovich, M P, Jones, J J, O'Toole, E A and Woodley, D T. (1999), NC1 domain of type VII collagen binds to the beta 3 chain of laminin 5 via a unique subdomain within the fibronectin-like repeats. J Invest Dermatol 112: 177-183.
32. Rousselle, P, Keene, D R, Ruggiero, F5 Champliaud, M F, Rest, M and Burgeson, R E. (1997). Laminin 5 binds the NC-I domain of type VII collagen. J Cell Biol 138: 719-728.
33. Hopkinson, I, Anglin, I E, Evans, D L and Harding, K G (1997). Collagen VII expression in human chronic wounds and scars. J Pathol 182: 192-196.
34. Chen, M, Petersen, M J, Li5 H-L, Cai, X-Y, OToole, E A and Woodley, D T (1997). Ultraviolet A irradiation upregulates type VII collagen expression in human dermal fibroblasts. J Invest Dermatol 108: 125-128.
35. Gammon, W R, Briggaman, R A, Inman III, A Q, Queen, L L and Wheeler, C E (1984). Differentiating anti-lamina lucida and anti-sublamina densa anti-BMZ antibodies by indirect immunofluorescence on 1.0M sodium chloride-separated skin. J Invest Dermatol 82: 139-144.
36. Keene, D R, Sakai, L Y, Lunstrum, G P, Morris, N P and Burgeson, R E (1987). Type VII collagen forms an extended network of anchoring fibrils. J Cell Bio 104: 611-621.
37. Champliaud, M F, Lunstrum, G P, Rousselle, P3 Nishiyama, T, Keene, D R and Burgeson, R E (1996). Human amnion contains a novel laminin variant, laminin 7, which like laminin 6, covalently associates with laminin 5 to promote stable epithelial-stromal attachment. J Cell Biol 132: 1189-1198.

What is claimed is:

1. A method for treating or accelerating healing of a wound in the skin of a subject having epidermolysis bullosa, comprising:
   intravenously administering to the subject having epidermolysis bullosa and the skin wound an effective amount of a pharmaceutical composition comprising recombinant human collagen type VII protein comprising an alpha chain having a collagenous triple-helical segment.

2. The method of claim 1, wherein the pharmaceutical composition is an injectable liquid formulation.

3. The method of claim 2, wherein the subject has a dystrophic form of epidermolysis bullosa (DEB).

4. The method of claim 2, wherein the subject has multiple skin wounds.

5. The method of claim 2, wherein the subject has chronic skin wounds.

6. The method of claim 1, wherein the pharmaceutical composition further comprises a stabilizing agent.

7. The method of claim 6, wherein the subject has a dystrophic form of epidermolysis bullosa (DEB).

8. The method of claim 6, wherein the subject has multiple skin wounds.

9. The method of claim 6, wherein the subject has chronic skin wounds.

10. The method of claim 1, wherein the subject has a dystrophic form of epidermolysis bullosa (DEB).

11. The method of claim 10, wherein the subject has multiple skin wounds.

12. The method of claim 10, wherein the subject has chronic skin wounds.

13. The method of claim 1, wherein the subject has multiple skin wounds.

14. The method of claim 1, wherein the subject has chronic skin wounds.

\* \* \* \* \*

UNITED STATES PATENT AND TRADEMARK OFFICE
CERTIFICATE OF CORRECTION

PATENT NO. : 10,711,052 B2
APPLICATION NO. : 13/657594
DATED : July 14, 2020
INVENTOR(S) : Mei Chen It is certified that error appears in the above-identified patent and that said Letters Patent is hereby corrected as shown below:

In the Specification

Column 1, Line 15, "STATEMENT OF FEDERALLY SPONSORED RESEARCH AND DEVELOPMENT" reads:
This invention was made, at least in part, with Govern-ment support under NIH grants RO-I AR 33625-22 and RO-I AR 4 7981-7. The Government has certain rights in the invention.

Should read:
This invention was made with government support under R01 AR047981, and R01 AR033625 awarded by the National Institutes of Health. The government has certain rights in the invention.

Signed and Sealed this
Nineteenth Day of November, 2024

Katherine Kelly Vidal
*Director of the United States Patent and Trademark Office*